United States Patent [19]

Coates

[11] Patent Number: 5,162,316

[45] Date of Patent: Nov. 10, 1992

[54] PYRIMIDO[4,5-D]PYRIMIDINE DERIVATIVES FOR USE AS BRONCHODILATORS

[75] Inventor: William J. Coates, Welwyn Garden City, England

[73] Assignee: Smith Kline & French Laboratories Limited, Welwyn Garden City, England

[21] Appl. No.: 669,691

[22] Filed: Mar. 13, 1991

Related U.S. Application Data

[63] Continuation of Ser. No. 365,341, Jun. 13, 1989, abandoned.

[30] Foreign Application Priority Data

Jun. 16, 1988 [GB] United Kingdom ............... 8814352

[51] Int. Cl.⁵ ............... A61K 31/505; C07D 487/02
[52] U.S. Cl. .................. 514/212; 514/234.2; 514/253; 514/256; 544/118; 544/256; 540/600
[58] Field of Search ............... 544/256, 118; 540/600; 514/212, 258, 253, 234.2

[56] References Cited

U.S. PATENT DOCUMENTS

| | | | |
|---|---|---|---|
| 3,074,928 | 1/1963 | Roch et al. | 544/118 |
| 3,138,592 | 6/1964 | Osdene | 540/600 |
| 3,830,812 | 8/1974 | Ramsey | 544/256 |
| 3,914,229 | 10/1975 | Martin et al. | 544/256 |
| 4,425,346 | 1/1984 | Horlington | 514/258 |
| 4,885,301 | 12/1989 | Coates | 544/265 |
| 5,034,393 | 7/1991 | Hackler | 544/256 |
| 5,047,404 | 9/1991 | Coates | 514/243 |

FOREIGN PATENT DOCUMENTS

| | | |
|---|---|---|
| A293063 | 11/1988 | European Pat. Off. |
| A347146 | 12/1989 | European Pat. Off. |
| A349239 | 1/1990 | European Pat. Off. |
| 1543874 | 4/1979 | United Kingdom |

OTHER PUBLICATIONS

Broughton et al., J. Med. Chem. vol. 18 pp. 1117–1122 (1975).
Graboyes et al., J. Med. Chem., 11, 568 (1968).
Weinstock et al., J. Med. Chem., 11, 573 (1968).
Davis et al. J. Cyclic Nucleotide Res. 5, 65–74 (1979).
Gupta et al., J. Heterocycl. Chem., 12, 1311 (1975).

*Primary Examiner*—Donald G. Daus
*Attorney, Agent, or Firm*—Charles M. Kinzig; Stephen Venetianer; Edward T. Lentz

[57] ABSTRACT

This invention relates to pyrimidopyrimidine derivatives which have bronchodilator and anti-allergic activities. A compound of the invention is 7-cyclopropylamino-4-oxo-2-(2-propoxyphenyl)-3,4-dihydropyrimido[4,5-d]pyrimidine.

11 Claims, No Drawings

PYRIMIDO[4,5-D]PYRIMIDINE DERIVATIVES FOR USE AS BRONCHODILATORS

This is a continuation of application Ser. No. 07/365,341 filed Jun. 13, 1989 now abandoned.

The present invention relates to pyrimidopyrimidine derivatives, intermediates in their preparation, pharmaceutical compositions containing them and a method of effecting bronchodilation or of combatting allergic diseases by administering them. The compounds of this invention are inhibitors of a calmodulin insensitive cyclic GMP phosphodiesterase and are of use in combatting such conditions where such inhibition is thought to be beneficial. They are bronchodilators and are therefore of use in combatting chronic reversible obstructive lung diseases such as asthma and bronchitis. Some of the compounds of the present inventions have anti-allergic activity and are therefore useful in combatting allergic diseases such as allergic asthma, allergic rhinitis, urticaria and irritable bowel syndrome. Furthermore the compounds of this invention are vasodilators and are therefore of value in combatting angina, hypertension and congestive heart failure.

Accordingly the present invention provides compounds of the formula (1):

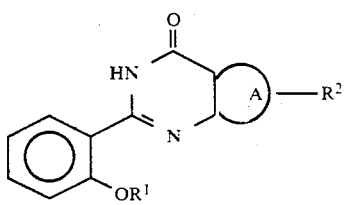

and pharmaceutically acceptable salts thereof, wherein $R^1$ is $C_{1-6}$alkyl, $C_{2-6}$alkenyl, $C_{3-5}$cycloalkyl$C_{1-6}$alkyl, or $C_{1-6}$alkyl substituted by 1 to 6 fluoro groups;

$R^2$ is $C_{1-6}$alkylthio, $C_{1-6}$alkylsulphonyl, $C_{1-6}$alkoxy, hydroxy, hydrogen, hydrazino, $C_{1-6}$alkyl, phenyl, —NHCOR$^3$ wherein $R^3$ is hydrogen or $C_{1-6}$alkyl, or —NR$^4$R$^5$, wherein $R^4$ and $R^5$ together with the nitrogen atom to which they are attached form a pyrrolidino, piperidino, hexahydroazepino, morpholino or piperazino ring, or $R^4$ and $R^5$ are independently hydrogen, $C_{3-5}$cycloalkyl or $C_{1-6}$alkyl which is optionally substituted by —CF$_3$, phenyl, —S(O)$_n$C$_{1-6}$alkyl wherein n is 0, 1 or 2, —OR$^6$, —CO$_2$R$^7$ or —NR$^8$R$^9$ wherein $R^6$ to $R^9$ are independently hydrogen or $C_{1-6}$alkyl, provided that the carbon atom adjacent to the nitrogen atom is not substituted by said —S(O)$_n$C$_{1-6}$-alkyl, —OR$^6$ or —NR$^8$R$^9$ groups; and

is a ring of sub-formula (a) or (b):

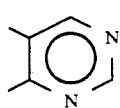

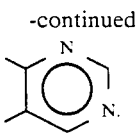

Suitably $R^1$ is $C_{2-5}$alkyl for example ethyl, n-propyl, isopropyl, butyl, isobutyl or pentyl.

Suitably $R^1$ is $C_{3-5}$alkenyl for example propenyl, butenyl or pentenyl.

Suitably $R^1$ is cyclopropylmethyl.

Examples of $C_{1-6}$alkyl substituted by 1 to 6 fluoro groups include —CF$_3$, —CH$_2$CF$_3$ or —CF$_2$CHFCF$_3$.

Preferably $R^1$ is n-propyl.

Suitably $R^2$ is $C_{1-6}$alkylthio, $C_{1-6}$alkylsulphonyl or $C_{1-6}$alkoxy for example methylthio, ethylthio, methylsulphonyl, ethylsulphonyl, methoxy, ethoxy or propoxy.

Suitably $R^2$ is hydroxy, hydrogen or hydrazino.

Suitably $R^2$ is phenyl or $C_{1-6}$alkyl for example methyl, ethyl or propyl.

Suitably $R^2$ is —NHCOR$^3$ for example formamido or acetamido.

Suitably $R^2$ is —NR$^4$R$^5$ for example amino, methylamino, ethylamino, propylamino, dimethylamino, diethylamino, dipropylamino, cyclopropylamino, morpholino, 2,2,2-trifluoroethylamino, phenethylamino, 3-methylthiopropylamino, 3-methylsulphinylpropylamino, 3-methylsulphonylpropylamino, 2-hydroxyethylamino, 3-hydroxypropylamino, 2-hydroxypropylamino, 3-methoxypropylamino, N-ethyl-N-(2-hydroxyethyl)amino, 2-aminoethylamino, 2-dimethylaminoethylamino, ethoxycarbonylmethylamino, carboxymethylamino, 2-ethoxycarbonylethylamino or 2-carboxyethylamino.

Suitably

is a group of sub-formula (a) thus forming a pyrimido[4,5-d]pyrimidine ring system.

Suitably

is a group of sub-formula (b) thus forming a pyrimido[5,4-d]pyrimidine ring system.

Particular compounds of this invention are:
7-methylthio-4-oxo-2-(2-propoxyphenyl)-3,4-dihydropyrimido[4,5-d]pyrimidine,
7-methylthio-2-(2-ethoxyphenyl)-4-oxo-3,4-dihydropyrimido[4,5-d]pyrimidine,
7-methylthio-2-(2-methoxyphenyl)-4-oxo-3,4-dihydropyrimido[4,5-d]pyrimidine,
7-methylthio-2-(2-isobutoxyphenyl)-4-oxo-3,4-dihydropyrimido[4,5-d]pyrimidine,
7-methylthio-2-(2-cyclopropylmethoxyphenyl)-4-oxo-3,4-dihydropyrimido[4,5-d]pyrimidine,
7-methylthio-2-(2-allyloxyphenyl)-4-oxo-3,4-dihydropyrimido[4,5-d]pyrimidine, 7-amino-4-oxo-2-(2-propoxyphenyl)-3,4-dihydropyrimido[4,5-d]pyrimidine,
7-methylamino-4-oxo-2-(2-propoxyphenyl)-3,4-dihydropyrimido[4,5-d]pyrimidine,
7-dimethylamino-4-oxo-2-(2-propoxyphenyl)-3,4-dihydropyrimido[4,5-d]pyrimidine,
7-hydrazino-4-oxo-2-(2-propoxyphenyl)-3,4-dihydropyrimido[4,5-d]pyrimidine,
4-oxo-2-(2-propoxyphenyl)-3,4-dihydropyrimido[4,5-d]pyrimidine,
7-ethylamino-4-oxo-2-(2-propoxyphenyl)-3,4-dihydropyrimido[4,5-d]pyrimidine,
7-(2-hydroxyethylamino)-4-oxo-2-(2-propoxyphenyl)-3,4-dihydropyrimido[4,5-d]pyrimidine,
7-ethyl-4-oxo-2-(2-propoxyphenyl)-3,4-dihydropyrimido[4,5-d]pyrimidine,
7-methylamino-2-(2-methoxyphenyl)-4-oxo-3,4-dihydropyrimido [4,5-d]pyrimidine,
7-phenyl-4-oxo-2-(2-propoxyphenyl)-3,4-dihydropyrimido[4,5-d]pyrimidine,
7-morpholino-4-oxo-2-(2-propoxyphenyl)-3,4-dihydropyrimido[4,5-d]pyrimidine,
7-cyclopropylamino-4-oxo-2-(2-propoxyphenyl)-3,4-dihydropyrimido[4,5-d]pyrimidine,
7-acetamido-4-oxo-2-(2-propoxyphenyl)-3,4-dihydropyrimido[4,5-d]pyrimidine,
7-propylamino-4-oxo-2-(2-propoxyphenyl)-3,4-dihydropyrimido [4,5-d]pyrimidine,
7-(3-hydroxypropylamino)-4-oxo-2-(2-propoxyphenyl)-3,4-dihydropyrimido[4,5-d]pyrimidine,
7-(2-methoxyethylamino)-4-oxo-2-(2-propoxyphenyl)-3,4-dihydropyrimido[4,5-d]pyrimidine,
7-(2-dimethylaminoethylamino)-4-oxo-2-(2-propoxyphenyl)-3,4-dihydropyrimido[4,5-d]pyrimidine,
7-(2-hydroxypropylamino)-4-oxo-2-(2-propoxyphenyl)-3,4-dihydropyrimido[4,5-d]pyrimidine,
7-(3-methylthiopropylamino)-4-oxo-2-(2-propoxyphenyl)-3,4-dihydropyrimido[4,5-d]pyrimidine,
7-(2-aminoethylamino)-4-oxo-2-(2-propoxyphenyl)-3,4-dihydropyrimido[4,5-d]pyrimidine hydrochloride,
7-(3-methylsulphinylpropylamino)-4-oxo-2-(2-propoxyphenyl)-3,4-dihydropyrimido[4,5-d]pyrimidine,
7-(3-methylsulphonylpropylamino)-4-oxo-2-(2-propoxyphenyl)-3,4-dihydropyrimido[4,5-d]pyrimidine,
4,7-dioxo-2-(2-propoxyphenyl)-3,4,7,8-tetrahydropyrimido-[4,5-d]pyrimidine,
7-methylsulphonyl-4-oxo-2-(2-propoxyphenyl)-3,4-dihydropyrimido[4,5-d]pyrimidine,
7-diethylamino-4-oxo-2-(2-propoxyphenyl)-3,4-dihydropyrimido[4,5-d]pyrimidine,
7-(2-ethoxycarbonylethylamino)-4-oxo-2-(2-propoxyphenyl)-3,4-dihydropyrimido[4,5-d]pyrimidine,
7-(ethoxycarbonylmethylamino)-4-oxo-2-(2-propoxyphenyl)-3,4-dihydropyrimido[4,5-d]pyrimidine,
7-(2-carboxyethylamino)-4-oxo-2-(2-propoxyphenyl)-3,4-dihydropyrimido[4,5-d]pyrimidine,
7-(carboxymethylamino)-4-oxo-2-(2-propoxyphenyl)-3,4-dihydropyrimido[4,5-d]pyrimidine,
7-ethoxy-4-oxo-2-(2-propoxyphenyl)-3,4-dihydropyrimido[4,5-d]pyrimidine,
7-methoxy-4-oxo-2-(2-propoxyphenyl)-3,4-dihydropyrimido-[4,5-d]pyrimidine,
7-(2,2,2-trifluoroethylamino)-4-oxo-2-(2-propoxyphenyl)-3,4-dihydropyrimido[4,5-d]pyrimidine,
7-propoxy-4-oxo-2-(2-propoxyphenyl)-3,4-dihydropyrimido-[4,5-d]pyrimidine,
7-(N-ethyl-N-hydroxyethylamino)-4-oxo-2-(2-propoxyphenyl)-3,4-dihydropyrimido[4,5-d]pyrimidine,
7-dipropylamino-4-oxo-2-(2-propoxyphenyl)-3,4-dihydropyrimido[4,5-d]pyrimidine,
7-(2-phenethylamino)-4-oxo-2-(2-propoxyphenyl)-3,4-dihydropyrimido[4,5-d]pyrimidine, or
4-oxo-2-(2-propoxyphenyl)-3,4-dihydropyrimido[5,4-d]pyrimidine,
or pharmaceutically acceptable salts thereof.

This invention covers all tautomeric and optical isomeric forms of compounds of formula (1).

Compounds of the formula (1) wherein $R^2$ is $-NR^4R^5$ or hydrazino may form pharmaceutically acceptable salts with acids such as hydrochloric, hydrobromic, sulphuric and phosphoric acids.

Compounds of the formula (1) may form pharmaceutically acceptable salts with metal ions, such as alkali metals for example sodium and potassium, or with an ammonium ion.

In order to use a compound of the formula (1) or a pharmaceutically acceptable salt thereof for the treatment of humans and other mammals it is normally formulated in accordance with standard pharmaceutical practice as a pharmaceutical composition.

Compounds of formula (1) and their pharmaceutically acceptable salts may be administered in standard manner for the treatment of the indicated diseases, for example orally, parenterally, transdermally, rectally, via inhalation or via buccal administration.

Compounds of formula (1) and their pharmaceutically acceptable salts which are active when given orally or via buccal administration can be formulated as liquids, syrups, tablets, capsules and lozenges. An oral liquid formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include starch, celluloses, lactose, sucrose and magnesium stearate. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

A typical suppository formulation comprises a compound of formula (1) or a pharmaceutically acceptable salt thereof which is active when administered in this way, with a binding and/or lubricating agent, for example polymeric glycols, gelatins, cocoa-butter or other low melting vegetable waxes or fats.

Typical transdermal formulations comprise a conventional aqueous or non-aqueous vehicle, for example a cream, ointment, lotion or paste or are in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane, or are in the form of a powder for insufflation.

Preferably the composition is in unit dosage form, for example a tablet, capsule or metered aerosol dose, so that the patient may administer to himself a single dose.

Each dosage unit for oral administration contains suitably from 0.001 mg/Kg to 30 mg/Kg, and preferably from 0.005 mg/Kg to 15 mg/Kg, and each dosage unit for parenteral administration contains suitably from 0.001 mg/Kg to 10 mg/Kg, of a compound of formula (1) or a pharmaceutically acceptable salt thereof calculated as the free base.

The daily dosage regimen for oral administration is suitably about 0.001 mg/Kg to 120 mg/Kg, of a compound of formula (1) or a pharmaceutically acceptable salt thereof calculated as the free base. The daily dosage regimen for parenteral administration is suitably about 0.001 mg/Kg to 40 mg/Kg, for example about 0.005 mg/Kg to 10 mg/Kg, of a compound of the formula (1) or a pharmaceutically acceptable salt thereof calculated as the free base. The active ingredient may be administered as required for example from 1 to 8 times a day or by infusion. The compositions of the invention are bronchodilators and are useful in chronic reversible obstructive lung disease for example asthma and bronchitis. In addition some of the compositions of the present invention have anti-allergic activity and are useful in combatting allergic diseases such as allergic asthma, allergic rhinitis, urticaria and irritable bowel syndrome. The compositions of the present invention also have vasodilator activity and are of use in the treatment of angina, hypertension and congestive heart failure. Such conditions can be treated by administration orally, topically, rectally, parenterally or by inhalation. For administration by inhalation dosages are controlled by a valve, are administered as required and for an adult are conveniently in the range 0.1–5.0 mg of a compound of the formula (1) or a pharmaceutically acceptable salt thereof.

The compounds of this invention may be co-administered with other pharmaceutically active compounds, for example in combination, concurrently or sequentially. Conveniently the compounds of this invention and the other active compound or compounds are formulated in a pharmaceutical composition. Examples of compounds which may be included in pharmaceutical compositions with the compounds of the formula (1) are bronchodilators such as sympathomimetic amines for example isoprenaline, isoetharine, sulbutamol, phenylephrine and ephedrine or xanthine derivatives for example theophylline and aminophylline, anti-allergic agents for example disodium cromoglycate, histamine $H_1$-antagonists, vasodilators for example hydralazine, angiotensin converting enzyme inhibitors for example captopril, anti-anginal agents for example isosorbide nitrate, glyceryl trinitrate and pentaerythritol tetranitrate, anti-arrhythmic agents for example quinidine, procainamide and lignocaine, calcium antagonists for example verapamil and nifedipine, diuretics such as thiazides and related compounds for example bendrofluazide, chlorothiazide, chlorothalidone, hydrochlorothiazide, and other diuretics for example frusemide and triamterene, and sedatives for example nitrazepam, flurazepam and diazepam.

The compounds of the formula (1) or pharmaceutically acceptable salts thereof can be prepared by a process which comprises:
 a) cyclising a compound of the formula (2):

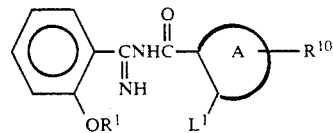

wherein $L^1$ is a displaceable group, $R^1$ and

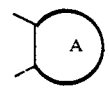

are as hereinbefore defined, and $R^{10}$ is a group $R^2$ as hereinbefore defined or a precursor thereof; or
 b) cyclising a compound of the formula (3):

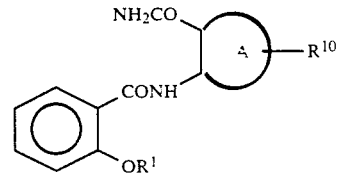

wherein $R^1$, $R^{10}$ and

are as hereinbefore defined; and thereafter where necessary:
 converting a group $R^{10}$ to a group $R^2$;
 optionally forming a pharmaceutically acceptable salt.

Suitably the cyclisation of a compound of the formula (2) is performed in the presence of a base such as an alkali metal carbonate or triethylamine, in an aprotic solvent such as dimethylformamide, acetonitrile or N-methylpyrrolidone, at ambient or an elevated temperature, for example 50°–170° C., conveniently at the reflux temperature of the reaction mixture. Suitably $L^1$ is halo for example bromo or chloro.

Suitably a compound of the formula (3) is cyclised by heating at an elevated temperature, for example 50°–150° C., in the presence of an acid or a base in a suitable solvent such as aqueous $C_{1-4}$alcohols, water, toluene, a halohydrocarbon or acetonitrile. Conveniently a compound of the formula (3) is cyclised by heating in pyridine or aqueous base such as sodium hydroxide at the reflux temperature of the reaction mixture.

Examples of $R^{10}$ being a precursor to a group $R^2$ is when $R^{10}$ is a halo or $C_{1-6}$alkylthio group. Such groups can be converted to a —$NR^4R^5$ group by reaction with an amine $HNR^4R^5$ in a suitable solvent such as a $C_{1-4}$-alkanol or pyridine at an elevated temperature, for example 50°–120° C., conveniently in a pressure vessel.

A compound of the formula (1) wherein $R^2$ is $C_{1-6}$alkylthio can suitably be converted to the corresponding compound wherein $R^2$ is $C_{1-6}$alkylsulphonyl by reaction with an oxidising agent, for example with at least two equivalents of a peroxy acid such as m-chloroperoxybenzoic acid.

A compound of the formula (1) wherein $R^2$ is $C_{1-6}$alkylsulphonyl can suitably be converted to the corresponding compound wherein $R^2$ is $-NR^4R^5$ by reaction with an amine $HNR^4R^5$ in a suitable solvent such as a halohydrocarbon or toluene at ambient or elevated temperature for example 40°-100° C.

A compound of the formula (1) wherein $R^2$ is $C_{1-6}$alkylsulphonyl can suitably be converted to the corresponding compound wherein $R^2$ is $C_{1-6}$alkoxy by reaction with a $C_{1-6}$alkoxide, eg. an alkali metal $C_{1-6}$alkoxide such as sodium methoxide or ethoxide, in a $C_{1-6}$alkanol at ambient or elevated temperature, for example 40°-100° C.

A compound of the formula (1) wherein $R^2$ is $C_{1-6}$alkylthio can suitably be converted to the corresponding compound wherein $R^2$ is hydrazino by reaction with hydrazine.

A compound of the formula (1) wherein $R^2$ is hydrazino can be converted to the corresponding compound wherein $R^2$ is hydrogen by treatment with silver oxide.

A compound of the formula (1) wherein $R^2$ is hydroxy can suitably be prepared by reacting a compound of the formula (1) wherein $R^2$ is $C_{1-6}$alkylthio with an alkali metal $C_{1-6}$alkoxide such as sodium methoxide or ethoxide under aqueous work-up conditions.

A compound of the formula (1) wherein $R^2$ is $C_{1-6}$alkoxy can be converted to the corresponding compound wherein $R^2$ is hydroxy by hydrolysis, for example by treatment with hydrochloric acid.

A compound of the formula (1) wherein $R^2$ is amino can suitably be converted to the corresponding compound where $R^2$ is $-NHCOR^3$ by reaction with a formylating or $C_{2-7}$alkanoylating agent. Examples of such reagents include formic acid, $C_{1-6}$alkyl formate, formamide, acetic anhydride, propionic anhydride or acetyl chloride.

A compound of the formula (1) wherein $R^4$ or $R^5$ is $C_{1-6}$alkyl substituted by $C_{1-6}$alkylthio can suitably be converted to the corresponding compound wherein $R^4$ or $R^5$ is $C_{1-6}$alkyl substituted by $C_{1-6}$alkylsulphinyl by reaction with one equivalent of an oxidising agent such as a peroxy acid, for example m-chloroperoxybenzoic acid. The $C_{1-6}$alkylsulphinyl compound can similarly be oxidised to a compound of the formula (1) wherein $R^4$ or $R^5$ is $C_{1-6}$alkyl substituted by $C_{1-6}$alkylsulphonyl.

A compound of the formula (1) wherein $R^4$ or $R^5$ is $C_{1-6}$alkyl substituted by $-CO_2R^7$ in which $R^7$ is $C_{1-6}$alkyl can suitably be hydrolysed by reaction with aqueous base, for example aqueous sodium hydroxide to form the corresponding compound wherein $R^7$ is hydrogen.

The compounds of the formula (2) can be prepared by reaction of a compound of the formula (4):

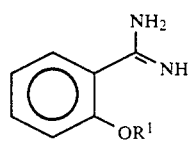
(4)

wherein $R^1$ is as hereinbefore defined, with a compound of the formula (5):

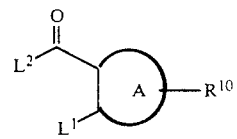
(5)

wherein $L^2$ is a leaving group and $L^1$, $R^{10}$ and

are as hereinbefore defined.

Suitably $L^2$ is $C_{1-6}$alkoxy or halo for example methoxy, ethoxy, chloro or bromo. Conveniently a solution of a compound of the formula (4) is initially formed by treatment of an acid addition salt of a compound of the formula (4) with a suitable base, for example triethylamine, a sodium alkoxide or sodium hydride, in an organic solvent such as a $C_{1-4}$alkanol, acetonitrile or dimethylformamide and the solution is then treated with a compound of the formula (5) at a moderate temperature for example 0°-60° C., conveniently ambient, to afford a compound of formula (2). Suitable acid addition salts are those formed with inorganic acids such as hydrochloric or sulphuric acid or with strong organic acids such as methanesulphonic or p-toluenesulphonic acid. Suitably a compound of the formula (2) is isolated and is then cyclised as hereinbefore described. Alternatively, a compound of the formula (2) is not isolated but is cyclised in situ by stirring at ambient or an elevated temperature, for example 40°-170° C.

A compound of the formula (3) can be prepared by reaction of a compound of the formula (6):

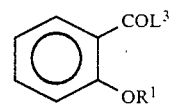
(6)

wherein $R^1$ is as hereinbefore defined and $L^3$ is halo, with a compound of the formula (7):

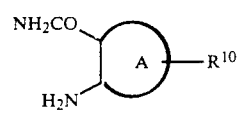
(7)

wherein $R^{10}$ and

are as hereinbefore defined.

Suitably $L^3$ is chloro or bromo. Suitably a compound of the formula (6) is reacted with a compound of the formula (7) at ambient or elevated temperature e.g. 50°-100° C. in a suitable solvent such as toluene, acetonitrile or a halohydrocarbon e.g. chloroform or dichloromethane, optionally in the presence of a base such as pyridine or triethylamine, to form a compound of the formula (3) which may be cyclised in situ or may be isolated and thereafter cyclised as hereinbefore described.

The compounds of the formula (4) and acid addition salts thereof are known or preparable in conventional manner from U.S. Pat. No. 3819631.

The compound of the formula (5) are known or can be prepared by methods known in the art.

For example a compound of the formula (5) wherein

is a group of sub-formula (a), $L^1$ is halo, $L^2$ is $C_{1-6}$-alkoxy and $R^{10}$ is in the 2-position of the pyrimidine ring can be prepared by reaction of a compound of the formula (8):

$$R^{10}\overset{NH}{\underset{\|}{C}}NH_2 \quad (8)$$

wherein $R^{10}$ is as hereinbefore defined, with a compound of the formula (9):

 (9)

wherein $R^{11}$ is $C_{1-6}$alkyl and $L^2$ is as hereinbefore defined, and thereafter by reaction with a halogenating agent.

Suitable halogenating agents include thionyl chloride, phosphorous oxychloride or phosphorous tribromide.

A compound of the formula (5) wherein

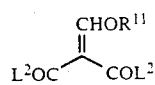

is a group of sub-formula (a), $L^1$ and $L^2$ are chloro and $R^{10}$ is 2-chloro can be prepared by reacting 2,4-dihydroxypyrimidine-5-carboxylic acid with phosphorous oxychloride.

A compound of the formula (5) wherein

is a group of sub-formula (a), $L^1$ is chloro, $L^2$ is ethoxy and $R^{10}$ is 2-methylthio is commercially available (Aldrich Chemical Co Ltd).

A compound of formula (5) wherein

is a group of sub-formula (b), $L^1$ is bromo, $L^2$ is chloro and $R^{10}$ is in the 2-position of the pyrimidine ring can be prepared by reaction of a compound of the formula (8) as hereinbefore defined with mucobromic acid and thereafter by reaction with a chlorinating agent such as thionyl chloride.

The compound of the formula (7) are known or can be prepared by methods known in the art.

For example a compound of the formula (7) wherein

is a group of sub-formula (a) and $R^{10}$ is in the 2-position of the pyrimidine ring can be prepared by hydrolysing a compound of the formula (10):

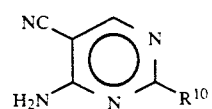 (10)

wherein $R^{10}$ is as hereinbefore defined.

Suitably a compound of the formula (10) is hydrolysed by treatment with concentrated sulphuric acid or by treatment with hydrogen peroxide and potassium hydroxide.

A compound of the formula (10) can be prepared by reacting a compound of the formula (8) as hereinbefore defined with a compound of the formula (11):

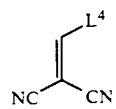 (11)

wherein $L^4$ is a leaving group.

Examples of $L^4$ include $C_{1-6}$alkoxy, $C_{1-6}$alkylthio or halo such as chloro or bromo. Suitably $L^4$ is $C_{1-6}$alkoxy.

Alternatively a compound of the formula (7) wherein

is a group of sub-formula (a) and $R^{10}$ is hydrogen can be prepared by reacting a compound of the formula (8) wherein $R^{10}$ is hydrogen with cyanoacetamide (Chem. Ber. 98, 3883 (1965)).

Pharmaceutically acceptable acid addition salts of the compounds of the formula (1) wherein $R^2$ is $-NR^4R^5$ or hydrazino may be prepared from the corresponding base of the compounds of the formula (1) in conventional manner. For example the base may be reacted with an acid in a $C_{1-4}$alkanol, or an ion-exchange resin may be used. The salts of the compounds of the formula (1) may be interconverted using ion-exchange resins. Non-pharmaceutically acceptable salts are therefore of use as they can be converted to pharmaceutically acceptable salts.

Pharmaceutically acceptable base addition salts of the compounds of the formula (1) may be prepared by standard methods, for example by reacting a solution of the compound of the formula (1) with a solution of the base.

The following biological test methods, data and Examples serve to illustrate this invention.

Bronchodilatation—In vivo

Male guinea-pigs of the Dunkin Hartley strain (500–600g) were anaesthetised with Sagatal (pentobarbital sodium) (60 mg/kg). Airway resistance was measured using a modification of the classical Konzett-Rossler technique (J. Pharm. Methods, 13, 309–315, 1985). U46619 (9,11-methaneoepoxy-PGH$_2$) was infused i.v. at a rate of 2.5 nmol/min, this produced a steady state of bronchoconstriction (approximately 120% increase from basal airway resistance). The compound under test was administered by i.v. bolus injection, and the subsequent peak inhibition of bronchoconstriction recorded.

The dose of compound required to reduce the U46619-induced bronchoconstriction by 50% is given as the BD$_{50}$. The compounds of Examples 1, 7, 8, 12, 13, 14, 18, 20, 21, 22 and 24 had BD$_{50}$ values in the range 0.48–3.85 μmol/kg. These results demonstrate in vivo antibronchoconstrictor activity.

Vasodilatation—In vivo

Male Wistar rats (300 g) were anaesthetised with a sodium 5-ethyl-5-(methylpropyl)-2-thiobarbiturate/-sodium pentobarbitone mixture i.p. (62.5 and 22.5 mg/kg respectively). The trachea was cannulated and the rats breathed spontaneously air enriched with O$_2$ (5 ml/min). Blood pressure was recorded from a carotid artery and a jugular vein was cannulated for the administration of compounds. The temperature of the animal was maintained at 37° C. by the use of an electric blanket. The abdominal aorta was separated from the inferior vena cava, distal to the renal arteries and was cannulated centrally to supply the perfusion pump with blood and distally for the perfusion of the hind quarters at constant pressure. The perfusion circuit was primed with 5% bovine serum albumin dissolved in 0.9% sodium chloride solution, pH adjusted to 7.4. Initially the pump rate was set between 10 and 15 ml/min to match the hind quarter perfusion pressure to that of the systemic circulation. Once set, the pressure remained unaltered for the rest of the experiment. A change in the speed of the pump (equivalent to hindquarter blood flow) was used to assess the changes in hindquarter vascular resistance. All compounds were administered as a bolus i.v. The compound of Example 1 caused a 43.7% increase in hindquarter blood flow at a dose of 50 μmol/kg.

Anti-allergic activity

Male Duncan Hartley guinea-pigs (250–300 g) were sensitised to ovalbumen by i.p. injection of 2 ml of 50mg.ml$^{-1}$ i.p. and 0.2 ml s.c. Three weeks later they were anaesthetised with 60mg.kg$^{-1}$ sodium pentabarbitone. The trachea was cannulated and the animal respired at a rate of 40 breaths per minute and at an initial tracheal inflation pressure of 16 mmHg. Tracheal inflation pressure was measured by a transducer connected to a side arm of the respiration circuit. The carotid artery was cannulated for the measurement of blood pressure and the signal was used to trigger an instantaneous rate meter. A jugular vein was cannulated for the administration of drug and allergen. After surgery the animals were allowed to stabilise and the drug was administered i.v. as a bolus. Following this, ovalbumen 1 mg.kg$^{-1}$ was injected i.v. as the antigen challenge either 2, 15 or 30 minutes following drug treatment and the peak bronchoconstrictor response recorded. For the control group ovalbumen only was given. One ovalbumen challenge per guinea-pig was used and n=6 for each time point. The percentage increase in tracheal inflation pressure was calculated. The following results indicating an anti-allergic activity were obtained.

| Compound of Example | Dose μmol/kg | % Inhibition of Control Bronchoconstrictor Response 30 min after drug administration |
| --- | --- | --- |
| 8 | 6.0 | 23 |
| 12 | 18.7 | 24 |
| 13 | 4.8 | 21 |
| 18 | 22.6 | 44 |
| 24 | 6.5 | 24 |

Phosphodiesterase activity

The activity of the compounds of the present invention as inhibitors of a calmodulin insensitive cyclic GMP phosphodiesterase was measured using the procedure described in European Patent Application No. 293063. The compounds of Examples 1 to 29 and 31 to 38 had IC$_{50}$ values (the concentration of inhibitor required for 50% inhibition of enzyme activity) in the range 0.2 to 27 μM. The compounds of the present invention have the advantage that they are selective in not inhibiting cyclic AMP phosphodiesterase (type III).

Inhibition of Phosphodiesterase (PDE)

Eight pig hearts/lungs were collected from the abattoir and kept on ice until the pulmonary arteries or aortas could be dissected and excess fat removed. 120 g of tissue was dissected. Unless otherwise stated, all procedures were done at 4° C. Following dissection, arteries were flash frozen in liquid nitrogen and stored at −70° C. until required. On the day of homogenisation, tissue was cooled with liquid nitrogen and broken into small pieces by striking with a hammer. The tissue was then homogenised in 15 mM BIS-TRIS, 1 μg/ml leupeptin and antipain, 2 μg/ml pepstatin A, 5 μM benzamide, 2 mM EDTA (ethylenediaminetetraacetic acid) and 2 mM dithiothreitol, pH 6.5. Phenylmethanesulphonylfluoride (PMSF) was added to a final concentration of 50 μM just prior to homogenisation. The homogenate was then centrifuged for 20 minutes at 30,000 g. Supernatant was filtered firstly through glass wool and then a 0.45 μm filter. The resultant filtrate was then applied to a 60 ml DEAE-Sepharose ® CL-6B (Diethylaminoethyl Cellulose with a bead size of 45–165 microns) (Pharmacia) column pre-equilibrated in homogenisation buffer. The column was washed with 150 mls of homogenisation buffer and PDE activities eluted with 150 ml of homogenisation buffer containing 100 mM sodium acetate. Six 25 ml fractions were collected. The flow rate throughout was 80 ml/hr.

Fractions 2 and 3 were pooled and BIS-TRIS, MgCl$_2$, CaCl$_2$ added to final concentrations of 50 mM, 7 mM and 5 mM respectively. PMSF, leupeptin, antipain and pepstatin A were also added at the concentrations described above for these components. The pH of this pooled sample was corrected to 6.9.

The sample was applied, at a flow rate of 3 ml/hr. to a tandem column set up. The first column in the tandem was a 5 ml calmodulin-agarose column (Sigma) and the second a 1.5 ml cibacron blue 3GA-agarose column (Sigma). Both columns were pre-equilibrated with 50 mM BIS-TRIS, 5 mM $MgCl_2$, 5 mM $CaCl_2$, 5 mM benzamidine, 2 mM dithiothreitol pH 6.9. Following application of the sample the columns were washed with 20 ml of equilibration buffer.

The cibacron blue-agarose column was then disconnected and washed with a variety of buffers as indicated below (Buffer A=50 mM BIS-TRIS, 5 mM benzamidine, 2 mM dithiothreitol pH 7.0).

20 ml Buffer A+2 M NaCl, 5 mM MgCl2
20 ml Buffer A+2 M NaCl
20 ml Buffer A+2 M NaCl, 10 mM EDTA PDE activity bound to the column was eluted with eight 2.5 ml aliquots of Buffer A containing 2 M NaCl, 10 mM EDTA and 10 mM cGMP. Fractions found to contain PDE activity were pooled and concentrated to approximately 1-3 the original volume by dialysis for 2 hr. against Buffer A glycerol (50:50) containing 15 mM 2-mercaptoethanol, 2 mM EDTA. After dialysis the concentration of cGMP in the fraction was reduced by treatment using a PD-10 column (Pharmacia) using dialysis buffer.

The fraction produced was stored at $-20°$ C. and for experiments diluted 50-fold and used as the source of PDE activity for the assay of compounds.

Properties of PDE activity

The PDE activity isolated by the procedure described above demonstrated considerable selectivity for cGMP as a substrate showing only poor rates of hydrolysis of cAMP. The PDE activity of this preparation could not be increased by the presence of $Ca^{2+}$ (10nM) and calmodulin (25 $\mu$g) in incubations and the hydrolysis of cAMP was not increased by the addition of 10 $\mu$M cGMP to incubations. The kinetic characteristics of this enzyme are summarised below.

$K_m$ cGMP = 1.3 $\mu$M
$K_m$ cAMP > 120 $\mu$M
Ratio of cGMP/cAMP hydrolysis at 1 $\mu$M substrate = 30

Phosphodiesterase Assay

The assay was as described by Davis & Daly (1979) J. Cyclic Nucleotide Res., 5, 65-74, but with some modifications. The standard reaction mixture contained in the final volume of
100 $\mu$l.50 $\mu$M 5'-GMP (including 4000 dpm $^4$C-GMP)
1 $\mu$M 3',5'-GMP (including 4000 dpm $^4$C-GMP)
10 $\mu$M enzyme preparation
10 $\mu$M inhibitor dilution
and buffered with 50 mM TRIS-5 mM $MgCl_2$ pH 7.5. The reaction was initiated with enzyme, and was carried out at 37° C. for 5-10 minutes. The reaction was terminated by placing tubes in a boiling water bath for 2 minutes. 500 $\mu$M of 0.1 M HEPES (N-2-hydroxyethylpiperazine-N'-2-ethanesulfonic acid) buffer pH 8.5 containing 0.1 M NaCl was then added to each assay tube and the contents applied to Affigel 601 (Bio-Rad) boronate affinity chromatography media (1.2 ml bed volume) which had previously been equilibrated with 10 ml of HEPES/NaCl buffer. Unreacted $^3$H-cGMP was washed from the column with 10-1 ml HEPES/NaCl buffer. Labelled 5'-AMP was eluted into a scintillation vial with 6 ml 0.25 M acetic acid and counted in a scintillation counter using 20 ml Instagel (Packard). Recoveries were between 50%-75% as measured by recovery of $^{14}$C-GMP. Assays were performed in duplicate and values corrected for blanks of <2%.

Calculation of IC$_{50}$ Values

IC$_{50}$ values (the concentration of inhibitor required for 50% inhibition of activity) were obtained by incubation of the enzymes at 1 $\mu$M cyclic GMP and a range of inhibitor concentrations.

EXAMPLE 1

7-Methylthio-4-oxo-2-(2-propoxyphenyl)-3,4-dihydropyrimido-[4.5-d]pyrimidine

2-Propoxybenzamidine (from sodium, 0.3 g, in ethanol, 50 ml, and 2-propoxybenzamidine hydrochloride, 2.77 g) was dissolved in 2-propanol (20 ml) and the resulting cooled (2° C.) solution was added to a cooled (2° C.) solution of ethyl 4-chloro-2-methylthio-5-pyrimidine carboxylate (2 g) in 2-propanol (30 ml). The reaction mixture was stirred at 2° C. for 2 hours and was then left overnight at ambient temperature to yield a white crude product, 1.18 g, m.p. 179°-181° C. Recrystallisation from ethanol yielded the title compound, 0.92 g, m.p. 186°-187° C.

EXAMPLE 2

7-Methylthio-2-(2-ethoxyphenyl)-4-oxo-3,4-dihydropyrimido[4,5-d]pyrimidine

2-Ethoxybenzamidine (from sodium, 0.08 g, in ethanol, 10 ml, and 2-ethoxybenzamidine hydrochloride, 0.70 g) was dissolved in acetonitrile (10 ml) and the resulting cooled (2° C.) solution was added to a cooled (2° C.) suspension of ethyl 4-chloro-2-methylthio-5-pyrimidine carboxylate (0.81 g) in acetonitrile (10 ml). The reaction mixture was stirred at 2° C. for one hour. Triethylamine (0.35 g) was added and the reaction mixture was stirred at ambient temperature for 21 hours to yield a white precipitate, 0.22 g, which was collected by filtration. The filtrate was reduced in volume under reduced pressure to yield a second crop of solid, 0.41 g. The products were combined and recrystallised from ethanol to yield the title compound, 0.30 g, m.p. 224.5°-225.5° C.

EXAMPLE 3

7-Methylthio-2-(2-methoxyphenyl)-4-oxo-3,4-dihydropyrimido[4,5-d]pyrimidine

2-Methoxybenzamidine (from sodium, 0.15 g, in ethanol, 20 ml, and 2-methoxybenzamidine methanesulphonate, 1.70 g) was dissolved in acetonitrile (20 ml) and the resulting cooled (2° C.) solution was added to a cooled (2° C.) suspension of ethyl 4-chloro-2-methylthio-5-pyrimidine carboxylate (2.33 g) in acetonitrile (20 ml). Triethylamine (0.66 g) was added and the reaction mixture was stirred at 2° C. for one hour and at ambient temperature for 18 hours. Acetonitrile was removed under reduced pressure and water (25 ml) was added. The mixture was cooled and a white solid was collected, washed with water and recrystallised from ethanol to yield the title compound, 0.46 g, m.p. 229°-231° C. (dec.).

EXAMPLE 4

7-Methylthio-2-(2-isobutoxyphenyl)-4-oxo-3,4-dihydropyrimido[4.5-d]pyrimidine Ethyl 4-chloro-2-methylthio-5-pyrimidine carboxylate (1.50 g) followed by triethylamine (0.65 g) was added to a stirred mixture of 2-isobutoxybenzamidine hydrochloride (1.46 g) and triethylamine (0.65 g) in acetonitrile (150 ml). The reaction mixture was stirred at 5° C. for 15 minutes and then at ambient temperature for 3 days. A solid (0.55 g) was collected by filtration and the filtrate was reduced in volume to yield a second crop of solid (0.47 g). The solids were combined and recrystallised from ethanol to yield the title compound, 0.57 g, m.p. 185°–186° C.

EXAMPLE 5

7-Methylthio-2-(2-cyclopropylmethoxyphenyl) 4-oxo 3,4-dihydropyrimido[4,5-d]pyrimidine In a similar manner to Example 4 reaction of ethyl 4-chloro-2-methylthio-5-pyrimidine carboxylate (1.50 g) with 2-cyclopropylmethoxybenzamidine hydrochloride (1.45 g) and triethylamine (1.30 g) in acetonitrile (50 ml) yielded a white solid (1.18 g) which was collected, dissolved in chloroform and the chloroform solution was extracted twice with 2 Normal hydrochloric acid. The chloroform solution was evaporated under reduced pressure and the residue was recrystallised from ethanol to yield the title compound, 0.52 g, m.p. 186°–187° C.

EXAMPLE 6

7-Methylthio-2 (2-allyloxyphenyl)-4-oxo-3,4-dihydropyrimido [4.5-d]pyrimidine 2-Allyloxybenzamidine (from sodium, 0.22 g, in ethanol, 100 ml, and 2 allyloxybenzamidine hydrochloride, 2.00 g) was dissolved in acetonitrile (50 ml) and the resulting cooled (2° C.) solution was added to a cooled (2° C.) solution of ethyl 4-chloro-2-methylthio-5-pyrimidine carboxylate (2.19 g) in acetonitrile (50 ml). The temperature was allowed to rise and the reaction mixture was stirred overnight at ambient temperature. The volume of the reaction mixture was reduced by evaporation under reduced pressure to yield a solid (0.96 g) which was collected. More product (0.45 g) precipitated from the filtrate. The combined products were recrystallised twice from ethanol to yield the title compound, 340 mg, m.p. 205°–206° C.

EXAMPLE 7

7 Amino 4-oxo-2-(2-propoxyphenyl)-3,4-dihydropyrimido[4.5-d]pyrimidine

7-Methylthio-4-oxo-2-(2-propoxyphenyl)-3,4-dihydropyrimido[4,5-d]pyrimidine (1.55 g) was heated in ethanolic ammonia (50 ml) in a pressure vessel for 8 hours at 90° C. and then for 8 hours at 145° C. After cooling a grey solid (0.64 g) was collected and was recrystallised from ethanol (with charcoal) to yield a crude product (0.47 g) which was recrystallised from ethanol to yield the title compound, 0.29 g, m.p. 261°–262° C.

EXAMPLE 8

7-Methylamino-4-oxo-2-(2-propoxyphenyl)-3,4-dihydropyrimido[4.5-d]pyrimidine 7-Methylthio-4-oxo-2-(2-propoxyphenyl)-3,4-dihydropyrimido[4,5-d]pyrimidine (1.40 g) was treated with a solution of methylamine in industrial methylated spirit (33%; 30 ml) in a pressure vessel for 9 hours at 90° C. The reaction mixture was evaporated under reduced pressure to yield a cream solid which was dissolved in chloroform. The organic solution was washed with water, dried (magnesium sulphate) and evaporated under reduced pressure to yield a cream solid. Elution from silica with chloroform:methanol (25:1) yielded a crude product which was recrystallised twice from ethanol to yield the title compound, 0.31 g, m.p. 235°–236° C.

EXAMPLE 9

7-Dimethylamino-4-oxo 2-(2-propoxyphenyl)-3,4-dihydropyrimido4,5-pyrimidine

7-Methylthio-4-oxo-2-(2-propoxyphenyl)-3,4-dihydropyrimido[4,5-d]pyrimidine (0.60 g) was treated with a solution of dimethylamine in industrial methylated spirit (33%; 20 ml) in a pressure vessel for 18 hours at 90° C. The cooled reaction mixture was evaporated under reduced pressure to yield a solid which was dissolved in aqueous sodium hydroxide. The filtered aqueous solution was neutralised with a few drops of concentrated hydrochloric acid to yield a pale yellow solid which was recrystallised from 2-propanol to yield the title compound, 0.33 g, m.p. 177.5°–178.5° C.

EXAMPLE 10

7-Hydrazino-4-oxo-2-(2-propoxyphenyl) 3,4-dihydropyrimido[4,5-d]pyrimidine

A stirred mixture of 7-methylthio-4-oxo-2-(2-propoxyphenyl)-3,4-dihydropyrimido[4,5-d]pyrimidine (1.31 g) and hydrazine hydrate (3 ml) in ethanol (30 ml) was heated under reflux for 3 hours to yield a yellow precipitate. The reaction mixture was cooled overnight and the yellow precipitate was collected and washed with ethanol and water to yield the title compound, 0.80 g, m.p. 219°–220° C.

EXAMPLE 11

4-Oxo 2-(2-propoxyphenyl)-3,4-dihydropyrimido[4,5-d]pyrimidine

A mixture of 7-hydrazino-4-oxo-2-(2-propoxyphenyl)-3,4-dihydropyrimido[4,5-d]pyrimidine (0.40 g) and silver oxide (0.32 g) in methanol (40 ml) was stirred at ambient temperature for 18 hours and at 45°–50° C. for 24 hours. The cooled reaction mixture was evaporated under reduced pressure and the residue was eluted from a silica column with chloroform. The combined fractions containing product were evaporated under reduced pressure to yield a white solid which together with another sample (27 mg), similarly prepared, was recrystallised from 2-propanol to yield the title compound, 136 mg, m.p. 142°–143° C.

EXAMPLE 12

7-Ethylamino-4-oxo-2-(2-propoxyphenyl)-3,4-dihydropyrimido[4,5-d]pyrimidine

In a similar manner to Example 9 reaction of 7-methylthio-4-oxo-2-(2-propoxyphenyl)-3,4-dihydropyrimido[4,5-d]pyrimidine (0.60 g) and 33% ethylamine in ethanol (20 ml) yielded the title compound, 0.29 g, m.p. 181°–182° C. (recrystallised from ethanol/water and then from ethanol).

EXAMPLE 13

7-(2-Hydroxyethylamino)-4-oxo-2-(2-propoxyphenyl)-3,4-dihydropyrimido4,5-d]pyrimidine A stirred mixture of 7-methylthio-4-oxo-2-(2-propoxyphenyl)-3,4-dihydropyrimido[4,5-d]pyrimidine (0.60 g) and ethanolamine (0.25 ml) in ethanol (20 ml) was heated under reflux for 19 hours. More ethanolamine (0.75 ml) was added and stirring under reflux continued for 16 hours. A white crystalline solid which precipitated from the cooled reaction mixture was collected, washed with cold ethanol and recrystallised from ethanol to yield the title compound, 0.38 g, m.p. 204°–205.5° C.

EXAMPLE 14

7-Ethyl-4-oxo-2-(2-propoxyphenyl)-3,4-dihydropyrimido[4,5-d]pyrimidine

In a similar manner to Example 3 reaction of ethyl 4-chloro-2-ethyl-5-pyrimidine carboxylate (0.86 g) with 2-propoxybenzamidine (from sodium, 0.1 g, in ethanol, 10 ml, and 2-propoxybenzamidine methanesulphonate, 1.20 g) and triethylamine (0.4 g) in acetonitrile (25 ml) for 3 days at ambient temperature yielded a crude product, which was recrystallised twice from 2-propanol-ether to yield the title compound, 95 mg, m.p. 118°–119° C.

EXAMPLE 15

7-Methylamino-2 (2-methoxyphenyl)-4-oxo-3,4-dihydropyrimido [4,5-d]pyrimidine

In a similar manner to Example 8 reaction of 7-methylthio-2-(2-methoxyphenyl)-4-oxo-3,4-dihydropyrimido[4,5-d]pyrimidine (0.75 g) and 33% methylamine in industrial methylated spirit (25 ml) for 18 hours yielded the title compound, 0.38 g, m.p. 265°–267° C. (recrystallised twice from methanol).

EXAMPLE 16

7-Phenyl-4-oxo-2-(2-propoxyphenyl) 3,4-dihydropyrimido[4.5-d]pyrimidine

In a similar manner to Example 3 reaction of ethyl 4-chloro-2-phenyl-5-pyrimidine carboxylate (1.05 g) with 2-propoxybenzamidine (from sodium, 0.10 g, in ethanol, 10 ml, and 2-propoxybenzamidine methanesulphonate, 1.20 g) and triethylamine (0.40 g) in acetonitrile (25 ml) for 3 days at ambient temperature yielded a crude product which was recrystallised from methanol to yield the title compound, 0.52 g, m.p. 203°–4° C.

EXAMPLE 17

7-Morpholino-4-oxo-2-(2-propoxyphenyl)-3,4-dihydropyrimido[4,5-d]pyrimidine

A stirred solution of 7-methylthio-4-oxo-2-(2-propoxyphenyl)-3,4-dihydropyrimido[4,5-d]pyrimidine (0.60 g) and morpholine (1.25 g) in pyridine (20 ml) was heated under reflux for 45 hours. The reaction mixture was evaporated under reduced pressure to yield a crude product which was washed with water and twice recrystallised from methanol to yield the title compound, 0.25 g, m.p. 175.5°–177° C.

EXAMPLE 18

7-Cyclopropylamino-4-oxo-2-(2-propoxyphenyl)-3,4-dihydropyrimido[4,5-d]pyrimidine A stirred mixture of 7-methylthio-4-oxo-2-(2-propoxyphenyl)-3,4-dihydropyrimido[4,5-d]pyrimidine (0.60 g) and cyclopropylamine (1.2 ml) in ethanol (20 ml) was heated for 18 hours at 90° C. in a pressure vessel. Further cyclopropylamine (1 ml) was added and the reaction mixture was stirred in a pressure vessel for 18 hours at 100° C. and then for 20 hours at 120° C. The cooled reaction mixture was evaporated under reduced pressure to yield a residue which was dissolved in 1 Normal sodium hydroxide. The resultant solution was treated with charcoal, filtered and the filtrate neutralised by the addition of concentrated hydrochloric acid which caused the precipitation of a crude product. The crude product was eluted from a silica column with chloroform as eluant, and the combined fractions containing product were evaporated under reduced pressure to yield a residue. This was twice recrystallised from methanol to yield the title compound, 0.23 g, m.p. 207.5°–208.5° C.

EXAMPLE 19

7-Acetamido-4-oxo-2-(2-propoxyphenyl)-3,4-dihydropyrimido[4.5-d]pyrimidine

A stirred mixture of 7-amino-4-oxo-2-(2-propoxyphenyl)-3,4-dihydropyrimido[4,5-d]pyrimidine (0.59 g)and acetic anhydride (5 ml) was heated under reflux for 1.5 hours Excess acetic anhydride was removed under reduced pressure. The solid residue was washed with water and triturated with hot methanol to yield the title compound, 0.57 g, m.p. 273°–4° C.

EXAMPLE 20

7-Propylamino-4-oxo-2-(2-propoxyphenyl)-3,4-dihydropyrimido[4,5-d]pyrimidine

In a similar manner to Example 9 reaction of 7-methylthio-4-oxo-2-(2-propoxyphenyl)-3,4-dihydropyrimido[4,5-d]pyrimidine (0.60 g) and n-propylamine (1.44 g) in ethanol (20 ml) yielded the title compound, 0.46 g, m.p. 185°–7° C. (recrystallised from ethanol).

EXAMPLE 21

7-(3-Hydroxypropylamino)-4-oxo-2-(2-propoxyphenyl)-3,4-dihydropyrimido[4.5 d]pyrimidine In a similar manner to Example 13, reaction of 7-methylthio-4-oxo-2-(2-propoxyphenyl)-3,4-dihydropyrimido[4,5-d]pyrimidine (0.45 g) and 3-amino-1-propanol (0.98 g) in ethanol (15 ml) yielded the title compound, 0.31 g, m.p. 185°–6° C. (recrystallised from ethanol).

EXAMPLE 22

7-(2-Methoxypropylamino)-4-oxo-2-(2-propoxyphenyl)-3,4-dihydropyrimido[4,5-d]pyrimidine In a similar manner to Example 13, reaction of 7-methylthio-4-oxo-2-(2-propoxyphenyl)-3,4-dihydropyrimido[4,5-d]pyrimidine (0.41 g) and methoxyethylamine (1.04 g) in ethanol (15 ml) for 48 hours yielded the title compound, 0.38 g, m.p. 193°-4° C. (recrystallised twice from methanol).

EXAMPLE 23

7-(2 Dimethylaminoethylamino)-4-oxo-2-(2-propoxyphenyl)-3,4-dihydropyrimido[4,5-d]pyrimidine In a similar manner to Example 13, reaction of 7-methylthio-4-oxo-2-(2-propoxyphenyl)-3,4-dihydropyrimido[4,5-d]pyrimidine (0.49 g) and N,N-dimethylethylenediamine (1.24 g) in ethanol (20 ml) yielded the title compound, 0.46 g, m.p. 181°-2° C. (recrystallised for methanol).

EXAMPLE 24

7-(2-Hydroxypropylamino)-4-oxo-2-(2-propoxyphenyl)-3,4-dihydropyrimido[4,5-d]pyrimidine In a similar manner to Example 13 reaction of 7-methylthio-4-oxo-2-(2-propoxyphenyl)-3,4-dihydropyrimido[4,5-d]pyrimidine (0.41 g) and 1-amino-2-propanol (0.97 g) in ethanol (15 ml) for 40 hours yielded the title compound 0.37 g, m.p. 212.5°-214° C. (recrystallised from methanol).

EXAMPLE 25

7-(3-Methylthiopropylamino)-4-oxo-2-(2-propoxyphenyl)-3,4-dihydropyrimido[4.5d]pyrimidine In a similar manner to Example 13 reaction of 7-methylthio-4-oxo-2-(2-propoxyphenyl)-3,4-dihydropyrimido[4,5-d]pyrimidine (0.79 g) and methylthiopropylamine (0.50 g) in ethanol (15 ml) for 40 hours yielded a crude product which was purified by elution from silica with 40°-60° petroleum ether:chloroform (gradient elution) to yield the title compound, 0.52 g, m.p. 173°-4° C. (recrystallised from methanol).

EXAMPLE 26

7-(2-Aminoethylamino)-4-oxo-2-(2-propoxyphenyl)-3,4-dihydropyrimido[4,5-d]pyrimidine hydrochloride A stirred solution of 7-methylthio-4-oxo-2-(2-propoxyphenyl)-3,4-dihydropyrimido[4,5-d]pyrimidine (0.49 g) and ethylenediamine (0.90 g) in ethanol (15 ml) was heated under reflux for 21 hours. Ethanol was removed under reduced pressure and the residue was dissolved in 1 Normal hydrochloric acid. The acidic solution was extracted with chloroform (3×10 ml), neutralised (to pH 6–7) with 2 Normal sodium hydroxide and evaporated under reduced pressure to yield a crude product which was recrystallised from methanol to yield the title compound, 0.28 g, m.p. 210°-2° C.

EXAMPLE 27

7-(3-Methylsulphinylpropylamino)-4-oxo-2-(2-propoxyphenyl)-3,4-dihydropyrimido[4.5 d]pyrimidine A cool (0° C.) solution of 7-(3-methylthiopropylamino)4-oxo-2-(2-propoxyphenyl)-3,4-dihydropyrimido[4,5-d]pyrimidine (1.84 g) and m-chloroperoxybenzoic acid (0.97 g) in dichloromethane (180 ml) was allowed to warm to ambient temperature with stirring. The solution was then stirred for 18 hours at ambient temperature and allowed to stand for 10 days. The reaction mixture was evaporated under reduced pressure and the residue eluted from a silica column with chloroform: methanol (gradient elution). The combined fractions containing product were evaporated under reduced pressure and the residue was recrystallised from isopropanol to yield the title compound, 1.73 g, m.p. 188°-9° C.

EXAMPLE 28

7-(3-Methylsulphonylpropylamino)-4-oxo-2-(2-propoxyphenyl)-3,4-dihydropyrimido[4.5-d]pyrimidine A solution of 7-(3-methylsulphinylpropylamino)-4-oxo-2-(2-propoxyphenyl)-3,4-dihydropyrimido[4,5-d]pyrimidine (0.80 g) and m-chloroperoxybenzoic acid (0.40 g) in dichloromethane (50 ml) was stirred at ambient temperature for 24 hours. During this time further m-chloroperoxybenzoic acid (about 200 mg) was added on 2 occasions. The solution was washed with dilute aqueous sodium bicarbonate (3×25 ml) and the combined washings back-extracted with a little dichloromethane. The combined organic layer was washed with water and then brine, dried (magnesium sulphate) and evaporated under reduced pressure to yield a residue. This was recrystallised three times from methanol to yield the title compound, 0.51 g, m.p. 222°-3° C.

EXAMPLE 29

4,7-Dioxo-2-(2-propoxyphenyl)-3,4,7,8-tetrahydropyrimido[4,5-d]pyrimidine

7-Methylthio-4-oxo-2-(2-propoxyphenyl)-3,4-dihydropyrimido[4,5-d]pyrimidine (0.66 g) and methanol (0.26 g) were added to a stirring suspension of sodium hydride (0.38 g, 50% suspension in oil) in dry dimethylsulphoxide (15 ml). The mixture was stirred at ambient temperature for 1.5 hours and at 70°-80° C. for 18 hours. The cooled reaction mixture was poured into water (500 ml), then glacial acetic acid (0.46 ml) was added and the mixture was extracted with chloroform (20o ml and then 2×100 ml). The combined extracts were washed with water, dried (magnesium sulphate) and evaporated under reduced pressure to yield a solid which was washed successively with ether and 40°-60° petroleum ether and recrystallised from dimethylformamide: water to yield a crude product (0.18 g). This together with another sample (0.24 g) similarly prepared was eluted from a silica column with chloroform and 10% methanol in chloroform. The combined fractions containing product were evaporated under reduced pressure and the residue recrystallised from dimethylformamide dilute hydrochloric acid and then from dimethylformamide to yield the title compound, 0.15 g, m.p. 271°-3° C. (decomposition).

EXAMPLE 30

7-Methylsulphonyl-4-oxo-2-(2-propoxyphenyl)-3,4-dihydropyrimido[4,5-d]pyrimidine A solution of 7-methylthio-4-oxo-2-(2-propoxyphenyl)-3,4-dihydropyrimido[4,5-d]pyrimidine (3.0 g) and m-chloroperoxybenzoic acid (3.8 g) in dichloromethane (180 ml) was stirred at ambient temperature for 3 hours and then allowed to stand for 3 days. The solution was washed with dilute aqueous sodium bicarbonate (3×75 ml) and the combined washings extracted with dichloromethane (2×25 ml). The combined organic layers were washed successively with water and brine, dried (magnesium sulphate) and evaporated under reduced pressure to yield a crude product which was recrystallised from acetonitrile to yield the title compound, 2.04 g, m.p. 217°–9° C.

EXAMPLE 31

7-Diethylamino-4-oxo-2-(2-propoxyphenyl)-3,4-dihydropyrimido[4,5-d]pyrimidine

A solution of 7-methylsulphonyl-4-oxo-2-(2-propoxyphenyl)-3,4-dihydropyrimido[4,5-d]pyrimidine (229 mg) and diethylamine (420 mg) in dichloromethane (8 ml) was stirred at ambient temperature for 3 hours. The reaction mixture was eluted from a silica column with diethyl ether:chloroform (4:1) and the combined fractions containing product were evaporated under reduced pressure to yield an oil which on trituration with 40°–60° petroleum ether yielded the title compound, 85.5 mg, m.p. 116°–7° C.

EXAMPLE 32

7-(2-Ethoxycarbonylethylamino)-4-oxo-2-(2-propoxyphenyl)3,4-dihydropyrimido[4,5-d]pyrimidine A solution of 7-methylsulphonyl-4-oxo-2-(2-propoxyphenyl)-3,4-dihydropyrimido[4,5-d]pyrimidine (1.0 g), β-alanine ethyl ester hydrochloride (1.10 g) and triethylamine (0.73 g) in dichloromethane (20 ml) was stirred at ambient temperature for 2.5 hours. The reaction mixture was extracted with dilute hydrochloric acid (20 ml) then water (10 ml), and the extracts back washed with dichloromethane (10 ml). The combined organic extracts were dried (magnesium sulphate) and evaporated under reduced pressure to yield a crude product which was recrystallised from ethanol: water to yield the title compound, 0.83 g, m.p. 142°–3° C.

EXAMPLE 33

7-(Ethoxycarbonylmethylamino)-4-oxo-2 (2-propoxyphenyl)-3,4-dihydropyrimido[4,5-d]pyrimidine In a similar manner to Example 32 reaction of 7-methylsulphonyl-4-oxo-2-(2-propoxyphenyl)-3,4-dihydropyrimido[4,5-d]pyrimidine (0.86 g), glycine ethyl ester hydrochloride (0.65 g) and triethylamine (0.47 g) in dichloromethane (15 ml) yielded the title compound, 0.38 g, m.p. 174.5°–176° C. (recrystallised from ethanol: water).

EXAMPLE 34

7-(2-Carboxyethylamino)-4-oxo-2-(2-propoxyphenyl)-3,4-dihydropyrimido[4,5-d]pyrimidine A solution of 7-(2-ethoxycarbonylethylamino)-4-oxo-2-(2-propoxyphenyl)-3,4 dihydropyrimido[4,5-d]pyrimidine (0.53 g) in 1 Normal sodium hydroxide (5 ml) was stirred at ambient temperature for 2 hours. Acidification of the reaction mixture with concentrated hydrochloric acid yielded a precipitate which was recrystallised from ethanol: water to yield the title compound, 0.42 g, m.p. 227°–8° C.

EXAMPLE 35

7-(Carboxymethylamino-4-oxo-2-(2-propoxyphenyl)-3,4-dihydropyrimido[4.5-d]pyrimidine In a similar manner to Example 34 reaction of 7-(ethoxycarbonylmethylamino)4-oxo-2-(2-propoxyphenyl)-3,4-dihydropyrimido[4,5-d]pyrimidine (0.54 g) and 1 Normal sodium hydroxide (5 ml) yielded the title compound 0.41 g, m.p. 252°–253.5° C. (dec.) (recrystallised from ethanol:water).

EXAMPLE 36

7-Ethoxy-4-oxo-2-(2-propoxyphenyl)-3,4-dihydropyrimido[4,5-d]pyrimidine

A solution of 7-methylsulphonyl-4-oxo-2-(2-propoxyphenyl)-3,4-dihydropyrimido[4,5-d]pyrimidine (0.50 g) in sodium ethoxide solution (from sodium, 0.16 g, and ethanol, 25 ml) was stirred at ambient temperature for 1.5 hours. Cooling and acidification of the reaction mixture with glacial acetic acid (0.42 g) yielded a precipitate which was twice recrystallised from ethanol to yield the title compound, 0.29 g, m.p. 196°–197.5° C.

EXAMPLE 37

7-Methoxy-4-oxo-2-(2-propoxyphenyl)-3,4-dihydropyrimido[4.5-d]pyrimidine

In a similar manner to Example 36 reaction of 7-methylsulphonyl-4-oxo-2-(2-propoxyphenyl)-3,4-dihydropyrimido[4,5-d]pyrimidine (0.50 g) and sodium methoxide solution (from sodium, 0.16 g, and methanol, 20 ml) yielded the title compound, 0.29 g, m.p. 231°–2°° C. (recrystallised from methanol).

EXAMPLE 38

7-(2,2,2-Trifluoroethylamino)-4-oxo-2-(2-propoxyphenyl)-3,4-dihydropyrmiio[4.5-d]pyrimidine A solution of 7-methylsulphonyl-4-oxo-2-(2-propoxyphenyl)-3,4-dihydropyrimido[4,5-d]pyrimidine (0.72 g), 2,2,2-trifluoroethylamine hydrochloride (0.97 g) and triethylamine (0.73 g) in dichloromethane (15 ml) was stirred at ambient temperature for 48 hours and allowed to stand for 4 days. A yellow solid had formed which was collected by filtration and washed with dichloromethane. The filtrate was washed with dilute hydrochloric acid (15 ml) then water (10 ml) and the aqueous layers extracted with dichloromethane (2×7.5 ml). The combined organic layers were dried (magnesium sulphate) and evaporated under reduced pressure to yield a crude product. This was eluted from a silica column with diethyl ether:chloroform (4:1) and the combined fractions containing product were evaporated under reduced pressure to yield a residue which was recrystallised from isopropanol to yield the title compound, 0.13 g, m.p. 214°–215.5° C.

EXAMPLE 39

7-Propoxy-4-oxo-2-(2-propoxyphenyl3,4-dihydropyrimido[4.5-d]pyrimidine

In a similar manner to Example 36 reaction of 7-methylsulphonyl-4-oxo-2-(2-propoxyphenyl)-3,4-dihydropyrimido[4,5-d]pyrimidine (0.54 g) and sodium propoxide solution (from sodium, 0.17 g, and n-propanol, 25 ml) yielded the title compound, 0.19 g, m.p. 157°–8° C. (recrystallised from n-propanol).

EXAMPLE 40

7-(N-Ethyl-N-hydroxyethylamino)-4-oxo-2-(2-propoxyphenyl)-3,4-dihydropyrimido[4.5-d]pyrimidine In a similar manner to Example 31 reaction of 7-methylsulphonyl-4-oxo-2-(2-propoxyphenyl)-3,4-dihydropyrimido[4,5-d]pyrimidine (0.40 g) and 2-(ethylamino)ethanol (0.64 g) in dichloromethane (12 ml)

yielded the title compound, 137 mg, m.p. 141°–2° C. (recrystallised from isopropanol-ether).

EXAMPLE 41

7-Dipropylamino-4-oxo-2-(2-propoxyphenyl)-3,4-dihydropyrimido[4,5-d]pyrimidine

In a similar manner to Example 31 reaction of 7-methylsulphonyl-4-oxo-2-(2-propoxyphenyl)-3,4-dihydropyrimido[4,5d]pyrimidine (0.40 g) and dipropylamine (0.74 g) in dichloromethane (10 ml) yielded the title compound, 88 mg, m.p. 123°–4° C. (recrystallised from cyclohexane).

EXAMPLE 42

7-(2-Phenethylamino)-4-oxo-2-(2-propoxyphenyl)-3,4-dihydropyrimido[4,5-d]pyrimidine In a similar manner to Example 31 reaction of 7-methylsulphonyl-4-oxo-2-(2-propoxyphenyl)-3,4-dihydropyrimido[4,5-d]pyrimidine (0.40 g) and phenethylamine yields the title compound.

EXAMPLE 43

Pharmaceutical compositions for oral administration are prepared by combining the following:

|  | % w/w |  |  |
| --- | --- | --- | --- |
| 7-Cyclopropylamino-4-oxo-2-(2-propoxyphenyl)-3,4-dihydropyrimido[4,5-d]pyrimidine | 0.5 | 3.0 | 7.14 |
| 2% w/w Soya lecithin in soya bean oil | 90.45 | 88.2 | 84.41 |
| Hydrogenated vegetable shortening and beeswax | 9.05 | 8.8 | 8.45 |

The formulations are then filled into individual soft gelatin capsules.

EXAMPLE 44

A pharmaceutical composition for parenteral administration is prepared by dissolving the title compound of Example 13 (0.02 g) in polyethylene glycol 300 (25 ml) with heating. This solution is then diluted with water for injections Ph. Eur. (to 100 ml). The solution is then sterilised by filtration through a 0.22 micron membrane filter and sealed in sterile containers.

What is claimed is:

1. A compound of the formula (1):

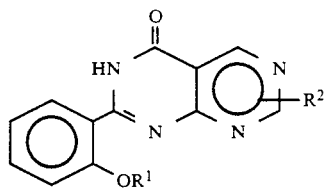

or a pharmaceutically acceptable salt thereof, wherein, $R^1$ is $C_{1-6}$alkyl, $C_{2-6}$alkenyl, $C_{3-5}$cycloalkyl$C_{1-6}$alkyl, or $C_{1-6}$alkyl substituted by 1 to 6 fluoro groups; $R^2$ is $C_{1-6}$alkylthio, $C_{1-6}$alkylsulphonyl, $C_{1-6}$alkoxy, hydroxy, hydrogen hydrazino, $C_{1-6}$alkyl, phenyl, —NHCOR$^3$ wherein $R^3$ is hydrogen or $C_{1-6}$alkyl, or —NR$^4$R$^5$, wherein $R^4$ and $R^5$ together with the nitrogen atom to which they are attached form a pyrrolidino, piperidino, hexahydroazepino, morpholino or piperazino ring, or $R^4$ and $R^5$ are independently hydrogen, $C_{3-5}$cycloalkyl or $C_{1-6}$alkyl which is optionally substituted by —CF$_3$, phenyl, —S(O)$_n$C$_{1-6}$alkyl wherein n is 0, 1 or 2, —OR$^6$, —CO$_2$R$^7$ or —NR$^8$R$^9$ where in R$^6$ to R$^9$ are independently hydrogen or C$_{1-6}$alkyl, provided that the carbon atom adjacent to the nitrogen atom is not substituted by said —S(O)$_n$C$_{1-6}$-alkyl, —OR$^6$ or —NR$^8$R$^9$ groups.

2. A compound according to claim 1 wherein $R^1$ is $C_{2-5}$alkyl.
3. A compound according to claim 1 wherein $R^1$ is n-propyl.
4. A compound according to claim 1 wherein $R^2$ is $C_{1-6}$alkylthio, $C_{1-6}$alkylsulphonyl or $C_{1-6}$alkoxy.
5. A compound according to claim 1 wherein $R^2$ is hydrogen, hydroxy or hydrazino.
6. A compound according to claim 1 wherein $R^2$ is phenyl or $C_{1-6}$alkyl.
7. A compound according to claim 1 wherein $R^2$ is —NHCOR$^3$ or —NR$^4$R$^5$.
8. A compound according to claim 1 which is selected from the group consisting of:
7-methylthio-4-oxo-2-(2-propoxyphenyl)-3,4-dihydropyrimido[4,5-d]pyrimidine,
7-methylthio-2-(2-ethoxyphenyl)-4-oxo-3,4-dihydropyrimido[4,5-d]pyrimidine,
7-methylthio-2-(2-methoxyphenyl)-4-oxo-3,4-dihydropyrimido[4,5-d]pyrimidine,
7-methylthio-2-(2-isobutoxyphenyl)-4-oxo-3,4-dihydropyrimido[4,5-d]pyrimidine,
7-methylthio-2-(2-cyclopropylmethoxyphenyl)-4-oxo-3,4dihydropyrimido[4,5-d]pyrimidine,
7-methylthio-2-(2-allyloxyphenyl)-4-oxo-3,4-dihydropyrimido[4,5-d]pyrimidine,
7-amino-4-oxo-2-(2-propoxyphenyl)-3,4-dihydropyrimido[4,5-d]pyrimidine,
7-methylamino-4-oxo-2-(2-propoxyphenyl)-3,4-dihydropyrimido[4,5-d]pyrimidine,
7-dimethylamino-4-oxo-2-(2-propoxyphenyl)-3,4-dihydropyrimido[4,5-d]pyrimidine,
7-hydrazino-4-oxo-2-(2-propoxyphenyl)-3,4-dihydropyrimido[4,5-d]pyrimidine,
4-oxo-2-(2-propoxyphenyl)-3,4-dihydropyrimido[4,5-d]pyrimidine,
7-ethylamino-4-oxo-2-(2-propoxyphenyl)-3,4-dihydropyrimido[4,5-d]pyrimidine,
7-(2-hydroxyethylamino)-4-oxo-2-(2-propoxyphenyl)-3,4-dihydropyrimido[4,5-d]pyrimidine,
7-ethyl-4-oxo-2-(2-propoxyphenyl)-3,4-dihydropyrimido[4,5-d]pyrimidine
7-methylamino-2-(2-methoxyphenyl)-4-oxo-3,4-dihydropyrimido[4,5-d]pyrimidine,
7-phenyl-4-oxo-2-(2-propoxyphenyl)-3,4-dihydropyrimido[4,5-d]pyrimidine,
7-morpholino-4-oxo-2-(2-propoxyphenyl)-3,4-dihydropyrimido[4,5-d]pyrimidine,
7-cyclopropylamino-4-oxo-2-(2-propoxyphenyl)-3,4-dihydropyrimido[4,5-d]pyrimidine,
7-acetamido-4-oxo-2-(2-propoxyphenyl)-3,4-dihydropyrimido[4,5-d]pyrimidine,
7-propylamino-4-oxo-2-(2-propoxyphenyl)-3,4-dihydropyrimido[4,5-d]pyrimidine,
7-(3-hydroxypropylamino)-4-oxo-2-(2-propoxyphenyl)-3,4-dihydropyrimido[4,5-d]pyrimidine,
7-(2-methoxyethylamino)-4-oxo-2-(2-propoxyphenyl)-3,4-dihydropyrimido[4,5-d]pyrimidine,
7-(2-dimethylaminoethylamino)-4-oxo-2-(2-propoxyphenyl)-3,4-dihydropyrimido[4,5-d]pyrimidine, 7-(2-hydroxypropylamino)-4-oxo-2-(2-propoxyphenyl)-3,4-dihydropyrimido[4,5-d]pyrimidine,
7-(3-methylthiopropylamino)-4-oxo-2-(2-propoxyphenyl)-3,4-dihydropyrimido[4,5-d]pyrimidine,
7-(2-aminoethylamino)-4-oxo-2-(2-propoxyphenyl)-3,4-dihydropyrimido[4,5-d]pyrimidine hydrochloride,
7-(3-methylsulphinylpropylamino)-4-oxo-2-(2-propoxyphenyl)-3,4-dihydropyrimido[4,5-d]pyrimidine,
7-(3-methylsulphonylpropylamino)-4-oxo-2-(2-propoxyphenyl)-3,4-dihydropyrimido[4,5-d]pyrimidine,
4,7-dioxo-2-(2-propoxyphenyl)-3,4,7,8-tetrahydropyrimido-[4,5-d]pyrimidine,
7-methylsulphonyl-4-oxo-2-(2-propoxyphenyl)-3,4-dihydropyrimido[4,5-d]pyrimidine,
7-diethylamino-4-oxo-2-(2-propoxyphenyl)-3,4-dihydropyrimido[4,5-d]pyrimidine,
7-(2-ethoxycarbonylethylamino)-4-oxo-2-(2-propoxyphenyl)-3,4-dihydropyrimido[4,5-d]pyrimidine,
7-(ethoxycarbonylmethylamino)-4-oxo-2-(2-propoxyphenyl)-3,4-dihydropyrimido[4,5-d]pyrimidine,
7-(2-carboxyethylamino)-4-oxo-2-(2-propoxyphenyl)-3,4dihydropyrimido[4,5-d]pyrimidine,
7-(carboxymethylamino)-4-oxo-2-(2-propoxyphenyl)-3,4dihydropyrimido[4,5-d]pyrimidine,
7-ethoxy-4-oxo-2-(2-propoxyphenyl)-3,4-dihydropyrimido[4,5-d]pyrimidine,
7-methoxy-4-oxo-2-(2-propoxyphenyl)-3,4-dihydropyrimido[4,5-d]pyrimidine,
7-(2,2,2-trifluoroethylamino)-4-oxo-2-(2-propoxyphenyl)-3,4-dihydropyrimido[4,5-d]pyrimidine,
7-propoxy-4-oxo-2-(2-propoxyphenyl)-3,4-dihydropyrimido[4,5-d]pyrimidine,
7-(N-ethyl-N-hydroxyethylamino)-4-oxo-2-(2-propoxyphenyl)-3,4-dihydropyrimido[4,5-d]pyrimidine,
7-dipropylamino-4-oxo-2-(2-propoxyphenyl)-3,4-dihydropyrimido[4,5-d]pyrimidine,
7-(2-phenethylamino)-4-oxo-2-(2-propoxyphenyl)-3,4-dihydropyrimido[4,5-d]pyrimidine, or
a pharmaceutically acceptable salt thereof.

9. A method of effecting bronchodilatation in a host in need thereof by administration of a non-toxic but effective amount of a compound according to claim 1.

10. A method of combatting allergic disease in a host in need thereof by administration of a non-toxic but effective amount of a compound according to claim 1.

11. A pharmaceutical composition comprising an effective amount of a compound according to claim 1 and a pharmaceutically acceptable carrier.

* * * * *